United States Patent [19]

Masuhara et al.

[11] Patent Number: 4,579,881

[45] Date of Patent: Apr. 1, 1986

[54] SOFT MATERIAL FOR LINING A DENTURE BASE

[75] Inventors: Eiichi Masuhara, 2-5-10 Hon-Komagome, Bunkyo-ku, Tokyo; Iwao Hayakawa, 2-17-15 Sannoh, Ohta-ku, Tokyo, both of Japan; Nobuo Bannai; Hideyuki Yasumi, both of Iwaki, both of Japan

[73] Assignees: Kureha Kagaku Kogyo Kabushiki Kaisha; Eiichi Masuhara; Iwao Hayakawa, all of Tokyo, Japan

[21] Appl. No.: 688,969

[22] Filed: Jan. 4, 1985

[30] Foreign Application Priority Data

Jan. 5, 1984 [JP] Japan ................................ 59-394

[51] Int. Cl.⁴ ..................... A61C 13/02; A61C 13/08; C08F 12/20; C08F 14/18
[52] U.S. Cl. .................................. 523/120; 526/249; 526/250; 526/254; 526/255; 525/276; 433/168.1; 433/171
[58] Field of Search .................. 106/35; 525/276; 526/249, 250, 254, 255; 433/168, 171; 523/109, 120

[56] References Cited

U.S. PATENT DOCUMENTS

| | | | |
|---|---|---|---|
| 1,990,903 | 2/1935 | Groff | 523/120 |
| 2,695,880 | 11/1954 | Benning et al. | 526/250 |
| 3,457,247 | 7/1969 | Katsushima et al. | 560/223 |
| 3,483,263 | 12/1969 | Schlichting et al. | 568/843 |
| 4,484,894 | 11/1984 | Masuhara et al. | 433/168 |

*Primary Examiner*—John Kight
*Assistant Examiner*—Nathan M. Nutter
*Attorney, Agent, or Firm*—Oblon, Fisher, Spivak, McClelland & Maier

[57] ABSTRACT

Disclosed herein is a soft, putty-like material for lining a denture base, comprising 100 parts by weight of a monomeric compound represented by the formula (I):

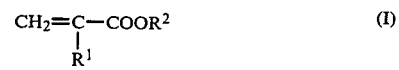

(I)

wherein $R^1$ represents a hydrogen atom or a methyl group and $R^2$ represents a residual group formed by removing a hydroxyl group from a fluorine-containing telomer having a molecular weight of less than 1500, 3 to 30 parts by weight of a fluorine-containing copolymer, 3 to 30 parts by weight of a $C_1$ to $C_{12}$-alkyl acrylate or methacrylate and 0.1 to 3.0 parts by weight of a polymerization-initiator.

4 Claims, No Drawings

SOFT MATERIAL FOR LINING A DENTURE BASE

BACKGROUND OF THE INVENTION

The present invention relates to a soft, putty-like material for lining a denture base, and in more detail, the present invention relates to a soft, putty-like material for lining a denture base, comprising 100 parts by weight of a monomeric compound represented by the formula (I):

wherein $R^1$ represents a hydrogen atom or a methyl group and $R^2$ represents a residual group formed by removing a hydroxyl group from a fluorine-containing telomer having a molecular weight of 200 to 1500, 3 to 30 parts by weight of a fluorine-containing copolymer, 3 to 30 parts by weight of a $C_1$ to $C_{12}$-alkyl acrylate or methacrylate and 0.1 to 3.0 parts by weight of a polymerization-initiator.

Although in a method for lining the inner surface of a denture base in order to moderate the occlusal pressure acting on the denture base and to transfer the moderated pressure to the mucous membrane surface in the oral cavity, various materials have been studied as the lining material, no adequate material for that purpose has been found.

In order to solve the above-mentioned problem, the present inventors have proposed a denture base lined with a fluoropolymer (refer to Japanese patent application Laying-Open No. 55-21919). The fluoropolymer lining material for a denture base scarcely absorbs water, is excellent in adhesiveness to the base material of the denture and does not deteriorate for a long time (longer than 2 years) of utilization in the oral cavity. However, the fluoropolymer lining material requires a more complicated operation in applying to a denture base than the commercialized materials and some problems still remain in the extent of softness thereof.

In order to solve the above-mentioned demerits, the present inventors have further proposed a method for lining a denture base with a soft material prepared by mixing the above-mentioned fluoropolymer with a fluorine-containing monomer obtained by bringing a fluorine-containing telomer having a molecular weight of not less than 1500 into esterification with acryloyl chloride or methacryloyl chloride and kneading the thus formed mixture disclosed in U.S. patent application Ser. No. 562,064, filed Dec. 16, 1983 and now abandoned and U.K. Patent Publication No. 2,132,209. Although the soft material used in this method exhibits an excellent effect as a material for moderating and transferring the occlusal pressure on the mucous membrane surface in the oral cavity or a material for stabilizing the denture base during a relatively short time of utilization in the oral cavity, there has still remained the following problem in the soft material in the case where the utilization of longer than one year is desired.

Namely, since the material has been softened by mixing the fluoropolymer with the fluorine-containing monomer, although the lining material has been remarkably improved in the processability, the softness of the material does not change after being lined onto the inner surface of the denture base and during the use of the thus lined denture base.

Accordingly, a flow of the thus lined material is induced by the occlusal pressure resulting in the gradual reduction of the thickness of the layer of the lined material and then in the disappearance of the layer of the lined material finally.

The present inventors have further studied in order to solve the just-mentioned problem. The object of the present invention is to provide a soft material having a fluidity in the stage of processing the material for lining and exhibiting an ideal hardness together with an elasticity after being applied as the lining.

SUMMARY OF THE INVENTION

In an aspect of the present invention, there is provided a soft, putty-like material for lining a denture base, comprising 100 parts by weight of a monomeric compound represented by the formula (I):

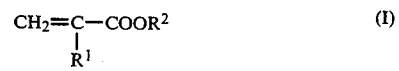

wherein $R^1$ represents a hydrogen atom or a methyl group and $R^2$ represents a residual group formed by removing a hydroxyl group from a fluorine-containing telomer having a molecular weight of 200 to 1500, 3 to 30 parts by weight of a fluorine-containing copolymer, 3 to 30 parts by weight of a $C_1$ to $C_{12}$-alkyl acrylate or methacrylate and 0.1 to 3.0 parts by weight of a polymerization-initiator.

DETAILED DESCRIPTION OF THE INVENTION

The soft, putty-like material according to the present invention (hereinafter referred to as the present material) is used for lining the inner surface of a denture base according to a conventional method.

The present material is applied on a doughy, rubbery methacrylic resin shaped in a gypsum mold and while applying a pressure thereonto by another gypsum mold and the thus pressed soft, putty-like material is heated, thereby polymerizing the components of the material to obtain a denture base which is made of the methacrylic resin and has the inner surface thereof lined with a soft copolymer showing an elasticity.

The soft putty-like material according to the present invention is excellent in processability, and does not require a specified operation in preparing a denture base according to the conventional method, because the putty-like material is very soft. The term "putty-like material" in the present invention includes the material of from a very viscous and sticky state to a putty-like state, and shows a penetration resistance of from 5 to 50 $g/mm^2$. In addition, after the polymerization the shore hardness of the surface of the thus lined material on the under surface of the denture base is preferably 10 to 30 (Shore D type, at 25° C.) and the lined material after the polymerization shows a modulus of rigidity of 5 to 50 $kg/cm^2$, a strength of adhesion to the surface of the denture base of 40 to 100 $kg/cm^2$ (fracture of a specimen occurs) and a water absorption of less than 0.2%.

Accordingly, the denture base lined with the present material exhibits a function of moderating the occlusal pressure and transferring the thus moderated occlusal pressure to the mucous membrane surface in the oral cavity and a good conformity between the denture base and the gingiva. Furthermore, such a denture base lined with the present material has a remarkable durability without showing no deterioration after having used for more than two years in the oral cavity.

The monomeric compound represented by the formula (I), which is one of the components of the present material can be produced according to the method disclosed in Japanese patent application Laying-Open No. 59-117503. Namely, a telomer is produced by subjecting a mixture of a fluorine-containing monomer as a taxogen and a primary alcohol as a telogen to telomerization in an autoclave in the presence of an organic peroxide such as diacyl peroxide, dialkyl peroxydicarbonate, etc. at a temperature of from 10° to 150° C., preferably 40 to 50° C., under an initial pressure of from 15 to 30 kg/cm$^2$, preferably 20 to 28 kg/cm$^2$ for from 8 to 12 hours, preferably 8 to 10 hours. The molar ratio of the telogen to the taxogen has a large influence on the molecular weight of the thus obtained telomer, and in order to have a telomer of a molecular weight of 200 to 1500 (preferably in the range of from 800 to 1200), the molar ratio is preferably in the range of from 3 to 7. In the case of the ratio of below 3, the molecular weight of the telomer becomes so large that solid telomer is formed other than the preferable oily telomer, and on the other hand, in the case of the ratio of over 7, the yield per batch of telomerization becomes smaller and it is disadvantageous.

As the taxogen, a mixture of at least two monomers selected from the group consisting of vinylidene fluoride, vinyl fluoride, trifluoroethylene, chloro-trifluoroethylene, tetrafluoroethylene and hexafluoropropylene is preferable, and particularly, a mixture comprising not less than 50% by weight of vinylidene fluoride as the main component is more preferable. In the case of using a telomer comprising vinylidene fluoride as the main component, the lining material having a more suitable pliability and an excellent durability is more easily available than in other cases.

In considering the pressure in telomerization, the reaction is preferably carried out at a temperature of from 40° to 50° C. in the presence of an initiator selected from dialkyl peroxydicarbonates for 8 to 10 hours.

After the telomerization is over, the reaction mixture of the autoclave is collected and the telogen is distilled out to obtain a telomer as a colourless, transparent and viscous liquid.

The thus obtained telomer is esterified to obtain the monomeric compound represented by the formula (I) as follows.

After dissolving the telomer in a solvent such as carbon tetrachloride, chloroform, etc, acrylic chloride or methacrylic chloride is added to the solution dropwise at a temperature of from 0° to 100° C. in 30 to 60 min. The esterification time is about 30 to 180 min. In the esterification, it is preferable to add a tertiary amine such as triethylamine for fixing the by-produced hydrogen chloride in the reaction system. The molar amount of the tertiary amine is preferably about 110% of that of the acid chloride.

Since the ester moiety of the monomeric compound represented by the formula (I) consists of the above-mentioned plural fluorine-containing telomer, the present material exhibits, after having been polymerized and solidified, an appropriate softness and an excellent durability and accordingly, the denture base lined with the thus soft, putty-like material does not show any deterioration even after more than 2 years of continued use thereof.

The fluorine-containing copolymer which is one of the components of the present material is made from at least two fluoro-olefinic monomers having 2 to 3 carbon atoms, preferably selected from the group consisting of vinylidene fluoride, vinyl fluoride, trifluoroethylene, chlorotrifluoroethylene, tetrafluoroethylene and hexafluoropropylene, and the rigidity of the fluorine-containing copolymer is preferably 10 to 150 kg/cm$^2$. Most preferable fluorine-containing copolymer is a terpolymer of 40 to 60% by weight of vinylidene fluoride and 20 to 30% by weight of two monomer selected from the group consisting of tetrafluoroethylene, chlorotrifluoroethylene and hexafluoropropylene.

Of the $C_1$ to $C_{12}$-alkyl acrylates or $C_1$ to $C_{12}$-alkyl methacrylates as one of the components of the present material, those having the alkyl group of 1 to 8 carbon atoms are preferable. Methyl acrylate, methyl methacrylate, ethyl acrylate, ethyl methacrylate, propyl acrylate, propyl methacrylate, butyl acrylate, butyl methacrylate, octyl acrylate, octyl methacrylate, 2-ethylhexyl acrylate and 2-ethylhexyl methacrylate may be mentioned.

As the polymerization initiator for use in the present invention, those organic peroxides of a long half life at room temperature such as benzoyl peroxide and di-t-butyl peroxide are preferable.

The amount of the fluorine-containing copolymer in the present material is in a range of 3 to 30 parts by weight, preferably 5 to 20 parts by weight to 100 parts by weight of the monomeric compound represented by the formula (I). The weight ratio is selected from the view points of (1) giving plasticity to the putty-like mixture for facilitating the processing operation and (2) giving strength to the layer of the solidified lining material after the polymerization. Namely, in the case where the amount of the fluorine-containing copolymer is below 3 parts by weight to 100 parts by weight of the amount of the monomeric compound represented by the formula (I), the viscosity of the thus formed putty-like mixture is so low that the processing of the putty-like mixture is a little difficult, and the strength of the solidified lining material after the polymerization is also low.

On the other hand, in the case where the amount of the fluorine-containing copolymer is over 30 parts by weight to 100 parts by weight of the monomeric compound represented by the formula (I), since the viscosity of the putty-like mixture is too high, the processing of the putty-like mixture is difficult, but the strength of the solidified lining material after the polymerization is high.

The amount of the $C_1$ to $C_{12}$-alkyl acrylate or $C_1$ to $C_{12}$-alkyl methacrylate in the present material is 3 to 30 parts by weight, preferably 5 to 20 parts by weight to 100 parts by weight of the monomeric compound represented by the formula (I) with the amount of the polymerization initiator of 0.1 to 3.0 parts by weight to 100 parts by weight of the monomeric compound represented by the formula (I). The purpose of the use of such an alkyl acrylate or methacrylate in such an amount is to disperse the polymerization initiator uniformly in the putty-like mixture and to adjust the strength and the hardness of the solidified lining material after the polymerization. Accordingly, in the case where the amount of such an alkyl acrylate or alkyl methacrylate is below 3 parts by weight to 100 parts by weight of the monomeric compound represented by the formula (I), the polymerization initiator is not uniformly dispersed in the present material. On the other hand, in the case where the amount is over 30 parts by weight to 100 parts by weight of the monomeric compound represented by the formula (I), although the strength of the solidified lining material after the polymerization is extremely high, the hardness thereof is too large to be used as a soft lining material after the polymerization. In addition, in order to adjust the hardness and the strength of the layer of the lining material after the polymerization, a cross-linking agent such as triethyleneglycol dimethacrylate and the like may be added to the present material before polymerization.

The present material is prepared as follows.

After adding the fluorine-containing copolymer to the monomeric compound represented by the formula (I) which is the major component of the present material, the mixture is kneaded at ordinary temperature or at an elevated temperature by heating thereof, preferably at 120° to 150° C. for carrying out the kneading effectively. Thereafter, in the case where the mixture is heated for kneading, the kneaded mixture is cooled to room temperature. After adding the alkyl acrylate or methacrylate containing the polymerization initiator dissolved therein to the kneaded mixture, the thus obtained mixture is well kneaded at room temperature to obtain the soft putty-like material which shows an appropriate softness (of 5 to 50 g/mm$^2$ in penetration resistance) and is extremely excellent in processability.

In preparing a denture base lined with the soft putty-like material, the thus prepared present material is stretched and pressure-welded, by the use of a doctor-knife or fingers, onto the surface of the doughy, rubbery acrylic resin shaped by the gypsum mold as in the case of preparing a denture base according to the conventional method, the surface facing the mucous membrane surface, and the present material and the acrylic resin are pressed by the conventional method and are polymerized by heating.

Then the monomeric compound represented by the formula (I) polymerizes to give a denture base having the inner surface lined with a soft resinous material showing elasticity.

The present invention will be explained more in detail while referring to the following non-limitative examples.

EXAMPLE 1

(1) Preparation of a Fluorine-Containing Telomer

After introducing 12 g of di-n-propyl peroxydicarbonate and 2,370 g (74.06 mol) of methanol into a 6-liter stainless-steel autoclave and replacing the air in the autoclave by gaseous nitrogen, the autoclave was cooled to about −30° C. in a methanol-dry ice bath, and 597 g (9.33 mol) of vinylidene fluoride, 358 g (3.07 mol) of chlorotrifluoroethylene and 239 g (2.39 mol) of tetrafluoroethylene were introduced thereinto (the weight ratio of the liquefied monomers is 50:30:20 in the order). After closing the autoclave, the resultant mixture was heated to 40° C. to initiate polymerization. The reaction was carried out for 8 hours at the same temperature under stirring. With the progress of polymerization, the inner pressure of the autoclave reduced from 24 kg/cm$^2$ to 4 kg/cm$^2$.

Then, the reaction was discontinued and the residual gases in the autoclave were released. The thus formed reaction mixture was distilled, thereby recovering methanol and obtaining a transparent oily substance.

The thus obtained oily substance was washed with water at 90° to 100° C. for decomposing and removing the residual organic peroxide, and after separation of the oily substance, it was distilled under a reduced pressure of 20 mmHg, thereby obtaining 1,027 g of a colourless and transparent fluorine-containing telomer of a molecular weight of 1,050 and of a viscosity of 7,500 cps at 25° C. in a yield of 86%.

(2) Preparation of a Monomeric Compound Represented by the Formula (I)

Into a round-bottomed flask provided with a stirrer, a reflux condenser and a dropping funnel, 12.6 g of methacryloyl chloride and 50 g of carbon tetrachloride, 100 g of the fluorine-containing telomer prepared in (1) and 15 g of triethylamine were introduced.

While keeping a water bath in which the flask was placed at a temperature of 80° C., the solution of methacryloyl chloride in carbon tetrachloride in the dropping funnel was added to the solution of the telomer under stirring in the flask drop by drop in 40 min. After stirring the mixture in the flask further for 30 min, 100 ml of water were added to the flask for dissolving the thus precipitated triethylamine hydrochloride, and stirring was continued for 10 min. After cooling the reaction mixture and collecting the thus separated oily layer, carbon tetrachloride was completely distilled off from the oily layer by steam distillation followed by distillation at 20 mmHg to obtain 102 g of one of the monomeric compound represented by the formula (I) wherein $R^1$ is a methyl group and $R^2$ is a residual group formed by removing a hydroxyl group from the fluorine-containing telomer comprising vinylidene fluoride, chlorotrifluoroethylene and tetrafluoroethylene in a weight ratio of 50:30:20 in the order and having a molecular weight of 1050.

(3) Preparation of a Soft, Putty-Like Material for Lining a Denture Base

In a mortar, 100 g of the monomeric compound obtained in (2) and 15 g of a soft copolymer of vinylidene fluoride, chlorotrifluoroethylene and tetrafluoroethylene in a weight ratio of 50:30:20 in the order, which shows a rigidity of 67 kg/cm$^2$, were mixed and the resultant mixture was heated in a thermostat at 160° C. At the time when the temperature of the mixture became 150° C., it was taken out of the thermostat and well kneaded for about 10 min, followed by cooling to room temperature.

Thereafter, a solution of 1 g of benzoyl peroxide in 15 g of methyl methacrylate was added to the thus cooled mixture, and the thus prepared mixture was kneaded at 25° C. (room temperature at the time). The kneading was carried out from the first state of a mixture of a liquid and a semi-solid to the final, uniform putty state as a mutual fusion of the two components, thereby obtaining a soft, putty-like material for lining a denture base. The interstitial resistance of the thus obtained present material (the hardness) was 7.5 g/mm$^2$.

(4) Preparation of a Denture Base Lined with the Soft, Putty-Like Material According to the Present Invention The thus obtained soft, putty-like material was applied in a conventional process for preparing a denture base made of acrylic resin and lined with the present material. Namely, the soft, putty-like material shaped in a form of a ribbon of about 10 cm in length, about 1.5 cm in width and 0.4 cm in thickness was lined on the inner surface of a denture base made of an acrylic resin by a pressure while stretching the material by a doctor-knife or fingers, and then the thus lined material was heated together with the denture base to 100° C., thereby causing polymerization of the monomers in the soft, putty-like material to obtain a denture base lined with the elastic and soft resin.

(5) Determination of the Elastic and Soft Resin Lining

After shaping the above-mentioned mixture of the monomeric compound, a soft copolymer of vinylidene fluoride, chlorotrifluoroethylene and tetrafluoroethylene, and methyl methacrylate as well as the polymerization initiator and polymerizing thereof between gypsum molds into test pieces of 36 mm in diameter and 7 mm in thickness, the Shore hardness (D) of the test piece was determined, the result being 23.

As a result of applying the denture base lined with the soft, putty-like material, which was prepared in (4), in an oral cavity of a man of 76 in age, any deterioration of the denture base was not observed even after actual use for 2 years, and the further continued use of the denture base was possible.

On the Level of the Penetration Resistance of the Present Material

After introducing 9 g of a test material in a compression cell of a tensilon tester and adjusting the temperature of the test material at 20° C., a stainless-steel rod of 2.3 mm in diameter was forced into the test material at a velocity of 100 mm/min, the level of resistance recorded on the recorder of the tensilon tester is the level of interstitial resistance shown by an unit of $g/mm^2$.

EXAMPLES 2 TO 9 AND COMPARATIVE EXAMPLES 1 TO 3

While using the same monomeric compound represented by the formula (I) prepared in (2) of Example 1, the soft, putty-like materials were prepared by changing the ratio of mixing thereof with the fluorine-containing copolymer and methyl methacrylate as shown in Table 1. The hardness of the thus obtained materials before polymerization and the hardness of the thus obtained materials after polymerization are shown also in Table 1.

As is seen from Table 1, the soft, putty-like materials of the present invention has an adequate softness and processability for lining, and after the polymerization, exhibits an ideal hardness together with an elasticity as the lining material for the denture base.

TABLE 1

| Example or Comparative Example | Mixing ratio A:B:C*[1] | Hardness of mixture ($g/mm^2$) | Hardness of after polymerization (Shore D) | Suitability[2] for Processing | Suitability[2] for As lining material |
|---|---|---|---|---|---|
| Example |  |  |  |  |  |
| 1 | 100:15:15 | 7.5 | 23 | A | A |
| 2 | 100:3:15 | 2.1 | 20 | B | A |
| 3 | 100:10:15 | 5.0 | 21 | A | A |
| 4 | 100:20:15 | 12.0 | 25 | A | A |
| 5 | 100:30:15 | 60.7 | 28 | B | B |
| 6 | 100:15:3 | 61.0 | 17 | B | A |
| 7 | 100:15:10 | 9.8 | 21 | A | A |
| 8 | 100:15:20 | 6.0 | 26 | A | A |
| 9 | 100:15:30 | 2.7 | 39 | B | B |
| Comparative Example |  |  |  |  |  |
| 1 | 100:1:15 | 0–1 | 19 | C | A |
| 2 | 100:40:15 | 240 | 32 | C | C |
| 3 | 100:15:40 | 1.0 | 45 | C | C |

Notes:
[1]Mixing ratio A:B:C means weight ratio of the monomeric compound represented by the formula (I):fluorine-containing copolymer:methyl methacrylate.
[2]A: suitable, B: less suitable and C: bad.

EXAMPLE 10

(1) Preparation of a fluorine-containing telomer

In the same procedures as in (1) of Example 1 except for using hexafluoropropylene instead of tetrafluoroethylene in Example 1, a telomer of a molecular weight of 980 comprising 50 parts by weight of vinylidene fluoride, 30 parts by weight of chlorotrifluoroethylene and 20 parts by weight of hexafluoropropylene was obtained.

(2) Preparation of a Monomeric Compound Represented by the Formula (I)

In the same procedures as in (2) of Example 1 except for using the fluorine-containing telomer prepared in (1) mentioned above, monomeric compound represented by the formula (I) wherein $R^1$ is a methyl group and $R^2$ is a residual group formed by removing a hydroxyl group from the fluorine-containing telomer comprising 50 parts by weight of vinylidene fluoride, 30 parts by weight of chlorotrifluoroethylene and 20 parts by weight of hexafluoropropylene was obtained.

(3) Preparation of a Soft, Putty-Like Material for Lining a Denture Base

In the same procedure as in (3) of Example 1 except for using 100 g of the fluorine-containing monomer obtained in (2) mentioned above and 20 g of a soft copolymer comprising 50 parts by weight of vinylidene fluoride, 30 parts by weight of chlorotrifluoroethylene and 20 parts by weight of hexafluoropropylene of rigidity of 62 $kg/cm^2$, and 10 g of methyl methacrylate, the soft, putty-like materials according to the present invention was obtained, which showed an interstitial resistance of 9.7 $g/mm^2$ before polymerization.

(4) Preparation of a Denture Base Lined with the Soft, Putty-Like Material According to the Present Invention In the same manner as in (4) of Example 1 except for using the soft, putty-like material obtained in (3) mentioned above instead of the soft, putty-like material obtained in Example 1, the denture base lined with the elastic and soft resin was prepared.

(5) Determination of the Elastic and Soft Resin Lining:

The Shore hardness (D) of the test piece made of the lining material obtained by (4) mentioned above was determined as in (5) of Example 1 and the Shore D was 22.5.

As a result of applying the denture base lined with the soft, putty-like material obtained in (4) mentioned above in an oral cavity of a man of 74 in age, any deterioration of the denture base was not observed even after 2 years of actual use thereof, and the further continued use thereof was possible.

EXAMPLE 11

(1) Preparation of a Fluorine-Containing Telomer

In the same procedures as in (1) of Example 1 except for using 180 g of tetrafluoroethylene and 418 g of hexafluoropropylene instead of 358 g of chlorotrifluoroethylene and 239 g of tetrafluoroethylene in Example 1, a fluorine-containing telomer comprising 50 parts by weight of vinylidene fluoride, 15 parts by weight of tetrafluoroethylene and 35 parts by weight of hexafluoropropylene of a molecular weight of 940 was obtained.

(2) Preparation of a Monomeric Compound Represented by the Formula (I)

In the same procedures as in (2) of Example 1 except for using the fluorine-containing telomer prepared in (1) mentioned above, the monomeric compound represented by the formula (I) wherein $R^1$ is a methyl group and $R^2$ is a residual group formed by removing a hydroxyl group from the telomer obtained in (1) mentioned above was obtained.

(3) Preparation of a Soft, Putty-Like Material for Lining a Denture Base

In the same manner as in (3) of Example 1 except for using 100 g of the monomeric compound obtained in (2) mentioned above and 10 g of 2-ethyl hexyl acrylate instead of the monomeric compound obtained in (2) and 15 g of methyl methacrylate of Example 1, still another of the soft, putty-like materials according to the present invention was obtained, which showed an interstitial resistance of 9.5 g/mm² before polymerization.

(4) Preparation of a Denture Base Lined with the Soft, Putty-Like Material According to the Present Invention In the same manner as in (4) of Example 1 except for using the soft, putty-like material obtained in (3) mentioned above instead of that obtained in Example 1, still another one of the denture bases lined with the elastic and soft resin was obtained.

(5) Determination of the Elastic and Soft Resin Lining

The Shore hardness (D) of the test piece made of the lining material obtained by (4) mentioned above was determined as in (5) of Example 1 and the Shore D was 24.

As a result of applying the denture base lined with the soft, putty-like material obtained in (4) mentioned above in an oral cavity of a man of 74 in age, any deterioration of the denture base was not observed even after 2 years of actual use thereof, and the further continued use thereof was possible.

EXAMPLE 12

(1) Preparation of a Monomeric Compound Represented by the Formula (I)

In the same procedures as in (2) of Example 1 except for using 10 g of acryloyl chloride and the fluorine-containing telomer obtained in (1) of Example 10 instead of 12.5 g of methacryloyl chloride and the fluorine-containing telomer obtained in (1) of Example 1, a monomeric compound represented by the formula (I) wherein $R^1$ is a hydrogen atom and $R^2$ is a residual group formed by removing a hydroxyl group from a telomer comprising 50 parts by weight of vinylidene fluoride, 30 parts by weight of chlorotrifluoroethylene and 20 parts by weight of hexafluoropropylene of a molecular weight of 1020 was obtained.

(2) Preparation of a Soft, Putty-Like Material for Lining a Denture Base

In the same manner as in (3) of Example 1 except for using the monomeric compound obtained in (1) mentioned above 15 g of ethylacrylate and 1 g of di-t-butyl peroxide as an initiator instead of the monomeric compound obtained in (2), 15 g of methyl methacrylate and 1 g of benzoyl peroxide as an initiator of Example 1, a soft, putty-like material for lining a denture base was prepared.

The interstitial resistance of the soft, putty material was 6.9 g/mm² before polymerization.

(3) Preparation of a Denture Base Lined with the Soft, Putty-Like Material According to the Present Invention In the same manner as in (4) of Example 1 except for using the soft, putty-like material obtained in (2) mentioned above instead of that obtained in Example 1, a denture base according to the present invention lined with the elastic and soft resin was obtained.

(4) Determination of the Elastic and Soft Resin Lining:

The Shore hardness (D) of the test piece made of the lining material obtained in (3) mentioned above was determined as in (5) of Example 1 and the Shore D was 22.

As a result of applying the thus prepared denture base lined with the soft, putty-like material obtained in (3) mentioned above in an oral cavity of a woman of 76 in age, any deterioration was not observed even after 2 years of actual use thereof, and the further continued use thereof was possible.

What is claimed is:

1. A soft, putty-like material for lining a denture base, comprising 100 parts by weight of a monomeric compound represented by the formula (I):

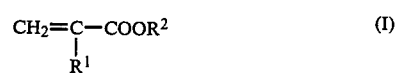

wherein $R^1$ represents a hydrogen atom or a methyl group and $R^2$ represents a residual group formed by removing a hydroxyl group from a fluorine-containing telomer having a molecular weight of 200 to 1500, 3 to 30 parts by weight of a fluorine-containing copolymer, 3 to 30 parts by weight of a $C_1$ to $C_{12}$-alkyl acrylate or methacrylate and 0.1 to 3.0 parts by weight of a polymerization-initiator.

2. A soft, putty-like material according to claim 1, wherein said fluorine-containing telomer is obtained by subjecting a mixture of at least two monomers selected from the group consisting of vinylidene fluoride, vinyl fluoride, trifluoroethylene, chlorotrifluoroethylene, tetrafluoroethylene and hexafluoropropylene to telomerization.

3. A soft, putty-like material according to claim 2, wherein the mixture contains not less than 50% by weight of vinylidene fluoride.

4. A soft, putty-like material according to claim 1, wherein said fluorine-containing copolymer comprises more than two monomers selected from the group consisting of vinylidene fluoride, vinyl fluoride, trifluoroethylene, chlorotrifluoroethylene, tetrafluoroethylene and hexafluoropropylene.

* * * * *